(12) United States Patent
Perrow

(10) Patent No.: US 10,779,956 B2
(45) Date of Patent: *Sep. 22, 2020

(54) SYSTEMS AND METHODS FOR INSERTING AN EXPANDABLE INTERVERTEBRAL DEVICE

(71) Applicant: Pioneer Surgical Technology, Inc., Marquette, MI (US)

(72) Inventor: Scott J. Perrow, Ishpeming, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/645,485

(22) Filed: Jul. 10, 2017

(65) Prior Publication Data

US 2017/0304070 A1     Oct. 26, 2017

Related U.S. Application Data

(63) Continuation of application No. 14/211,569, filed on Mar. 14, 2014, now Pat. No. 9,700,430.

(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4455* (2013.01); *A61F 2/4611* (2013.01); *A61F 2002/3012* (2013.01); *A61F 2002/30125* (2013.01); *A61F 2002/30131* (2013.01); *A61F 2002/30285* (2013.01); *A61F 2002/30398* (2013.01);

(Continued)

(58) Field of Classification Search
CPC ................... A61F 2/447; A61F 2/4455; A61F 2002/4627; A61F 2002/4475; A61F 2002/30579; A61F 2002/30398

See application file for complete search history.

(56) References Cited

U.S. PATENT DOCUMENTS

| | | | | |
|---|---|---|---|---|
| 5,554,191 A | * | 9/1996 | Lahille ............... | A61B 17/1671 411/55 |
| 6,039,761 A | * | 3/2000 | Li .......................... | A61B 17/70 623/17.16 |

(Continued)

OTHER PUBLICATIONS

Park et al, Kambin's Triangle Approach of Lumbar Transforaminal Epidural Injection with Spinal Stenosis, Dec. 30, 2011 (10 pages).

*Primary Examiner* — Ellen C Hammond
*Assistant Examiner* — Tara Rose E Carter
(74) *Attorney, Agent, or Firm* — Fitch, Even, Tabin & Flannery LLP

(57) ABSTRACT

An expandable interbody device for implantation within an intervertebral space is provided, together with methods and tools for use therewith. The interbody devices of the present invention include upper and lower bearing members configured to expand via an expansion mechanism configured to allow the insertion of osteoconductive materials and other structures into the interior of the interbody device before and after implantation, and before and after expansion of the interbody device. The insertion tool is configured expand the interbody device and to allow insertion of materials into the interbody device through a protected pathway.

20 Claims, 14 Drawing Sheets

Related U.S. Application Data

(60) Provisional application No. 61/798,736, filed on Mar. 15, 2013.

(52) U.S. Cl.
CPC .............. *A61F 2002/30556* (2013.01); *A61F 2002/30579* (2013.01); *A61F 2002/30593* (2013.01); *A61F 2002/30797* (2013.01); *A61F 2002/30904* (2013.01); *A61F 2002/4627* (2013.01)

(56) References Cited

U.S. PATENT DOCUMENTS

| | | | |
|---|---|---|---|
| 6,193,757 B1 | 2/2001 | Foley et al. | |
| 6,443,989 B1 * | 9/2002 | Jackson | A61F 2/4455 606/247 |
| 6,641,614 B1 * | 11/2003 | Wagner | A61F 2/4455 623/17.15 |
| 6,716,247 B2 * | 4/2004 | Michelson | A61F 2/4455 623/17.11 |
| 6,893,464 B2 | 5/2005 | Kiester | |
| 7,217,293 B2 | 5/2007 | Branch, Jr. | |
| 7,883,542 B2 | 2/2011 | Zipnick | |
| 8,062,375 B2 | 11/2011 | Glerum et al. | |
| 8,105,382 B2 | 1/2012 | Olmos et al. | |
| 8,133,232 B2 | 3/2012 | Levy et al. | |
| 8,163,026 B2 | 4/2012 | Gray | |
| 8,685,031 B2 | 4/2014 | Kleiner et al. | |
| 8,709,088 B2 | 4/2014 | Kleiner et al. | |
| 8,888,854 B2 | 11/2014 | Glerum et al. | |
| 8,906,028 B2 | 12/2014 | Kleiner et al. | |
| D723,682 S | 3/2015 | Kleiner et al. | |
| D750,249 S | 2/2016 | Grimberg, Jr. et al. | |
| 9,522,070 B2 * | 12/2016 | Flower | A61L 27/32 |
| 9,700,430 B2 | 7/2017 | Perrow | |
| 2003/0074063 A1 * | 4/2003 | Gerbec | A61F 2/447 623/16.11 |
| 2003/0208275 A1 * | 11/2003 | Michelson | A61F 2/4455 623/17.16 |
| 2004/0087947 A1 * | 5/2004 | Lim | A61F 2/4465 606/247 |
| 2005/0010295 A1 * | 1/2005 | Michelson | A61F 2/446 623/17.11 |
| 2005/0149048 A1 | 7/2005 | LePort et al. | |
| 2005/0278036 A1 * | 12/2005 | Leonard | A61F 2/442 623/23.47 |
| 2011/0172774 A1 | 7/2011 | Varela | |
| 2011/0282453 A1 | 11/2011 | Greenhalgh | |
| 2012/0029637 A1 * | 2/2012 | Ragab | A61F 2/447 623/17.11 |
| 2014/0094917 A1 * | 4/2014 | Salerni | A61F 2/447 623/17.16 |
| 2014/0249631 A1 | 9/2014 | Weiman | |
| 2016/0106551 A1 | 4/2016 | Grimberg, Jr. et al. | |

* cited by examiner

SYSTEMS AND METHODS FOR INSERTING AN EXPANDABLE INTERVERTEBRAL DEVICE

CROSS-REFERENCE TO RELATED APPLICATION

This application is a continuation of U.S. application Ser. No. 14/211,569, filed Mar. 14, 2014, which claims the benefit of U.S. Provisional Application No. 61/798,736, filed Mar. 15, 2013, both of which are hereby incorporated by reference in their entireties herein.

FIELD OF THE INVENTION

This invention pertains generally to implantable medical devices and, in particular, to expandable implantable devices for intervertebral fusion and/or immobilization and systems and methods for inserting the same.

BACKGROUND OF THE INVENTION

Many people develop back pain during the course of their life due to traumatic injury, disease, or genetic defect. Typically, the patients' intervertebral discs, which support the spine, are damaged, causing the discs to bulge or herniate. The disc bulge then impinges on the nerves of the spine and causes back pain. Surgeons often perform a discectomy to trim the disc bulge to alleviate back pain. However, the discectomy may structurally weaken the disc and often leads to subsequent structural failure of the disc due to wear and aging, once again causing impingement on the nerves of the spine and back pain. Surgical implantation of a medical implant device to structurally support and separate the vertebrae may become desirable to end debilitating back pain and allow patients to regain normal life activities.

One known device for promoting fusion between adjacent vertebrae is an expandable interbody device (IBD). Such devices are generally configured to be inserted into the intervertebral space in a compact configuration, and then are expanded to an expanded configuration to restore the adjacent vertebrae to a desired spacing. Numerous mechanisms are known for expanding the height of an expandable IBD, such as a threaded screw which drives one or more wedge members against ramped surfaces to drive the outer surfaces of the IBD apart. (See e.g., U.S. Pat. No. 8,105,382). It is also known to provide an IBD with one or more openings in the top and bottom outer surfaces of the IBD for containing bone graft material to promote fusion between the vertebrae to stabilize the joint.

One disadvantage of known expandable IBDs is that the expansion mechanisms materially constrain or limit the area in which bone graft material may be contained. The expansion mechanisms often occupy the central part of the IBD, leaving little or no space for bone graft material. Further, it is difficult or impossible with known expandable IBDs to add bone graft material after the IBD is implanted between the vertebrae. While some expandable IBDs may be configured to hold bone graft material for promoting fusion, once the device is expanded, there may not be sufficient bone graft material to fill the bone graft cavity in the device such that sufficient bone graft material is kept in contact with the adjacent vertebral endplate to adequately promote bone ingrowth. In such cases, a safe and effective manner to insert additional bone graft material after insertion of the IBD into the intervertebral space is desirable.

Thus, it would be advantageous to provide an expandable interbody device for implantation in the intervertebral space between vertebral bodies for supporting and/or spacing apart the vertebral bodies and having improved characteristics for promoting bone growth and fusion therebetween and/or immobilization thereof. It would further be advantageous to provide a system for safely and effectively inserting bone graft material into the intervertebral device after the device has been inserted into the intervertebral space. The present invention may be used to provide these and other benefits, as will be apparent from the following description of embodiments of the present invention.

SUMMARY OF THE INVENTION

In accordance with one aspect of the invention, an interbody device for implantation within an intervertebral space between adjacent vertebrae is provided. The implant device includes an implant body that is expandable in at least one direction. In one form the implant body includes upper and lower bearing members that are expandable between a compact configuration and an expanded configuration. The bearing members are operably connected to an expansion mechanism operable to allow at least one of the bearing members to move with respect to the other.

In one form, the upper and lower bearing members each have a bone-engaging outer surface and an inner facing surface, a distal leading end, a proximal trailing end, and opposing lateral sides. In each bearing member, a through-opening extends between the bone-engaging outer surface and the inner facing surface, and is located between the leading and trailing ends and the opposing lateral sides. The through-openings allow boney ingrowth between the adjacent vertebrae.

The expansion mechanism is operably connected to the upper and lower bearing members and is configured to permit shifting of the bearing members between a compact configuration and an expanded configuration. In one form, the expansion mechanism located between the upper and lower bearing members and on either side of the through-opening in each of the upper and lower bearing members with the through-openings generally being oriented so as to provide a substantially uninterrupted void between the outer surfaces of the upper and lower bearing members to promote boney ingrowth between the adjacent vertebrae.

In another form according to the present invention, a system for implanting an interbody device between adjacent upper and lower vertebrae is provided. The system includes an expandable interbody device having upper and lower bearing members and an opening at a proximal end thereof for insertion of osteoconductive material. In addition, various structural components may be inserted, such as a plug configured for inserting an osteoconductive material, such as a bone graft or other biologic material, or a spacer for maintaining the height of the expandable interbody device. The system preferably includes an insertion tool configured to hold the expandable interbody device, including an actuator for causing the interbody device to expand and a hollow shaft assembly. The hollow shaft assembly is preferably configured to provide an enclosed pathway through the shaft assembly to the opening in the proximal end of the expandable interbody device for inserting bone graft material or additional components into the interior of the expandable interbody device while the insertion tool is engaged with the interbody device.

A method of inserting an expandable intervertebral device according to one aspect of the present invention includes the steps of preparing an intervertebral disc for implantation of an interbody device, inserting the interbody device into the intervertebral space with an insertion tool, expanding the interbody device into an expanded configuration with the insertion tool, and inserting osteoconductive material through an enclosed path of the insertion tool into the interbody device while the insertion tool is engaged with the interbody device. In one form of the invention, the interbody device is sized and configured in the unexpanded state to be implanted into the intervertebral space laterally.

Additional advantages and features of the invention will become apparent from the following description and attached claims taken in combination with the accompanying drawings.

DETAILED DESCRIPTION OF THE PREFERRED EMBODIMENTS

Figure 1:
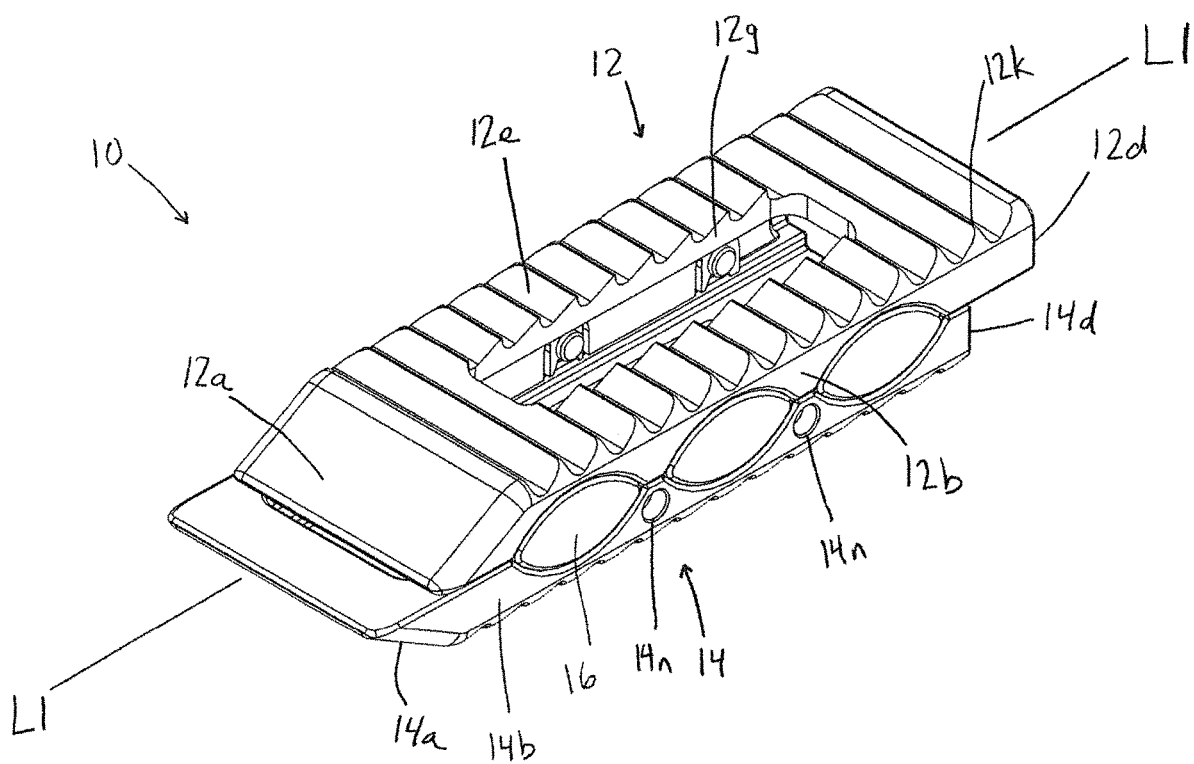
FIG. 1 is a perspective view of an expandable interbody device in a compact configuration in accordance with one aspect of the invention.
Figure 2:
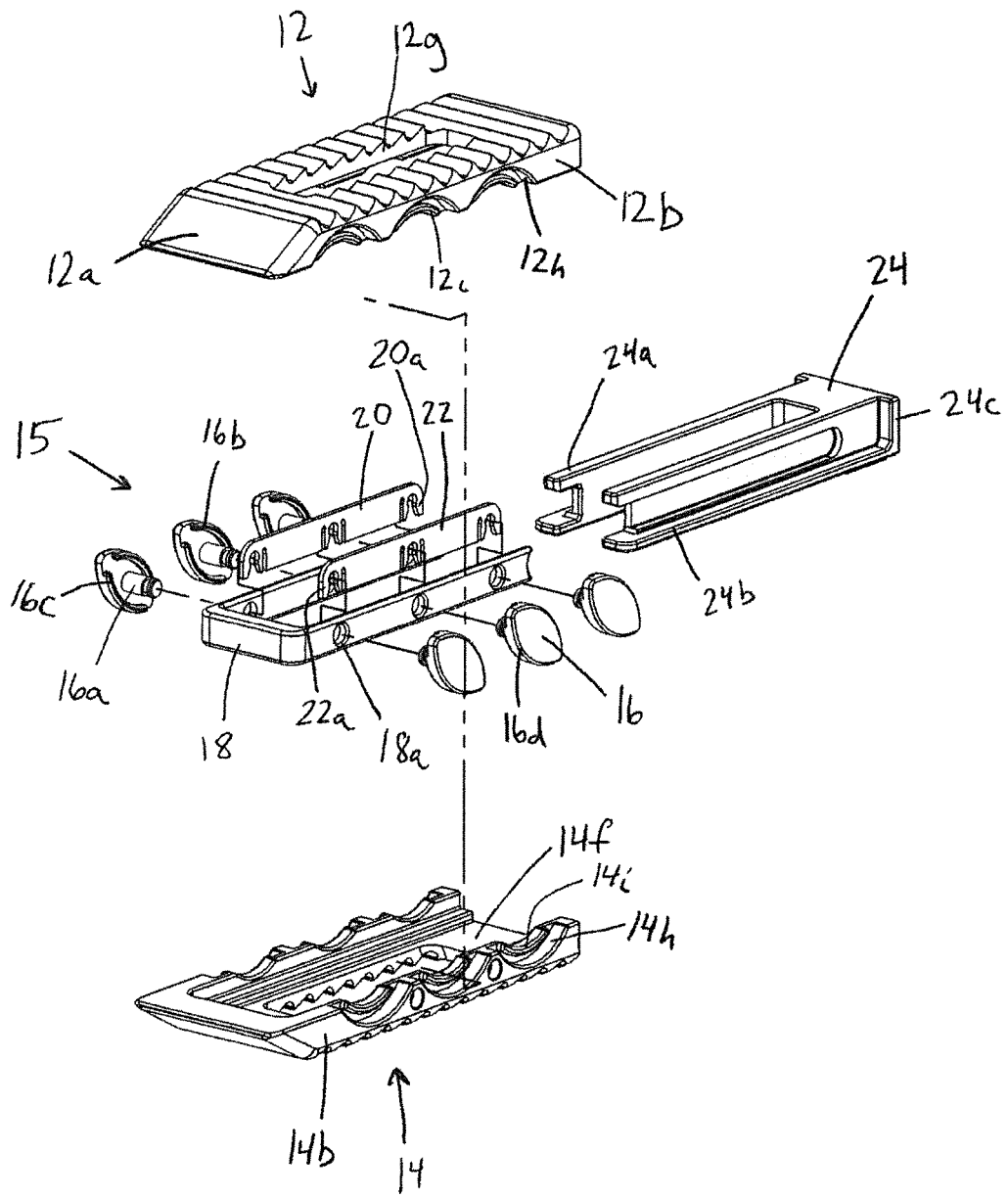
FIG. 2 is an exploded perspective view of the interbody device of FIG. 1.
Figure 3:
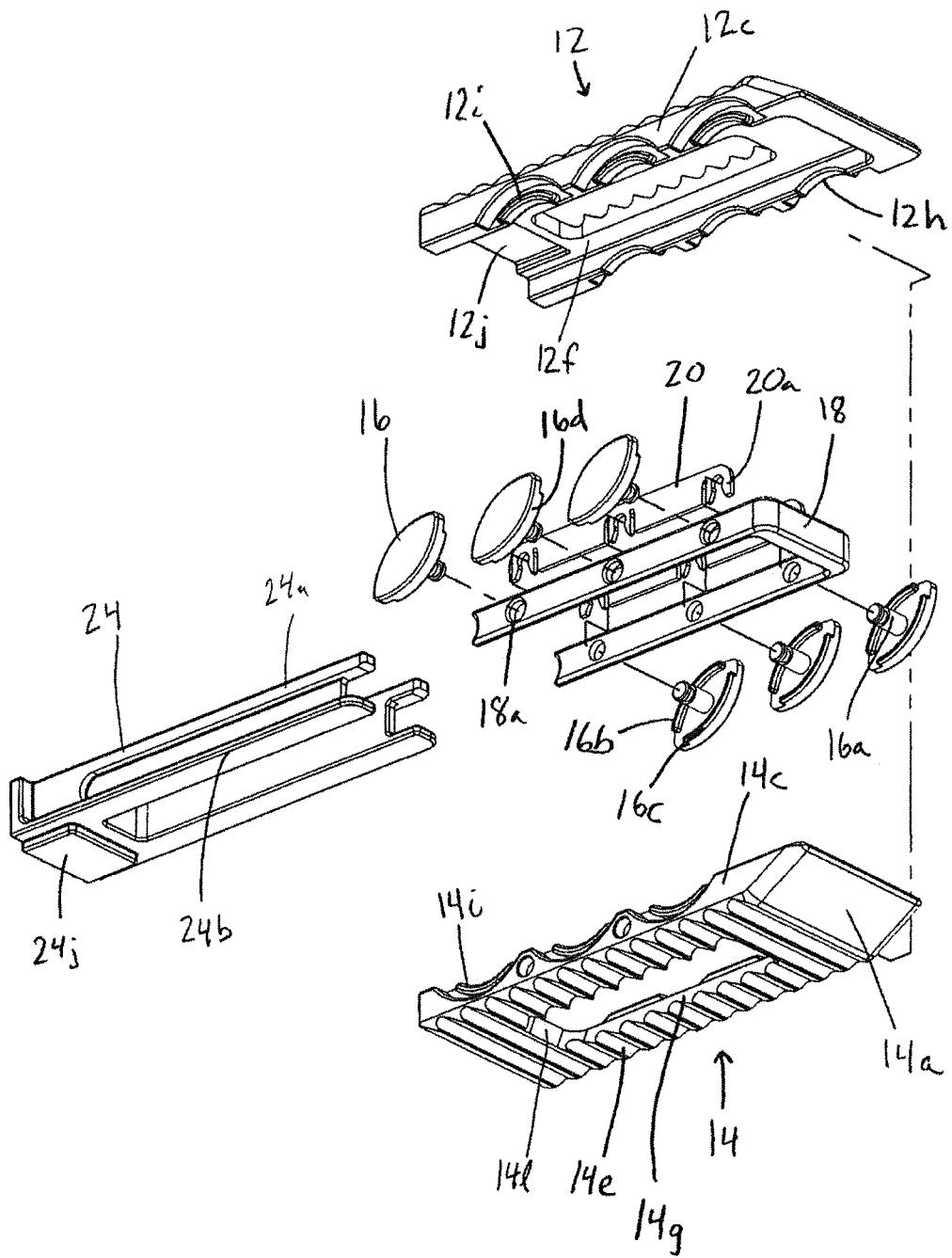
FIG. 3 is an alternate exploded perspective view of the interbody device of FIG. 1.

With reference to FIGS. 1-3 in accordance with one aspect of the invention, an expandable interbody device 10 has upper and lower bearing members 12, 14 configured to be implanted in the intervertebral space between adjacent vertebrae. The upper and lower bearing members are expandably connected to one another via an expansion mechanism 15, which in this embodiment includes slide cam members 16 having a substantially elliptical or football shape. Each upper and lower bearing member has a generally rectangular shape with a distal leading end 12a, 14a having a sloped or tapered configuration for promoting ease of insertion. The bearing members 12, 14 each have opposing lateral sides 12b, 12c, 14b, 14c and proximal trailing ends 12d, 14d. In addition, each bearing member has bone or endplate engaging outer surfaces 12e, 14e, inner facing surfaces 12f, 14f, and a recess or through-opening 12g, 14g that extend between and opens to the outer and inner facing surfaces. As will be described in more detail herein, the various components of the interbody device 10 are configured to promote boney ingrowth into and through the interbody device for stabilizing the joint after implantation of the device 10.

Figure 6:
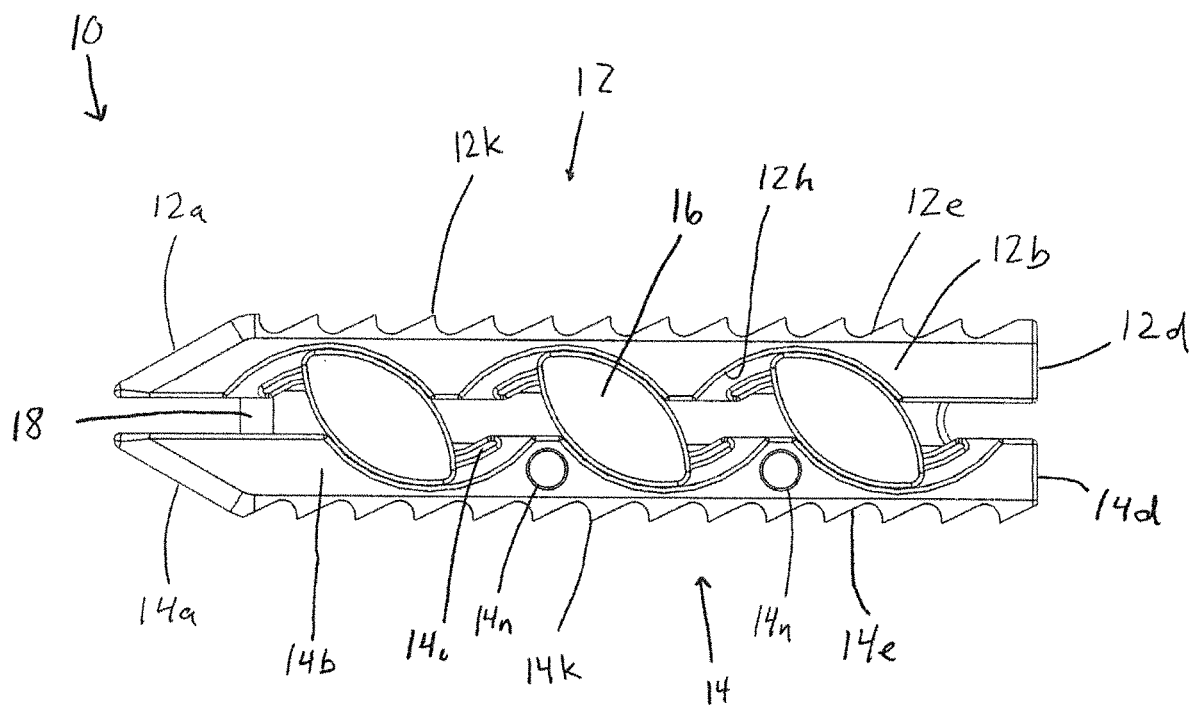
FIG. 6 is a side view of the interbody body device of FIG. 1 in the fully expanded configuration.

The outer surfaces 12e, 14e of the interbody device are preferably configured to resist movement once implanted and to resist expulsion from the intervertebral space. For example, as shown in FIG. 6, the upper bearing member 12 comprises projections, such as teeth 12k that are configured to resist migration in one direction, and the outer surface 14e of the lower bearing member 14 comprises projections, such as teeth 14k, that are configured to resist migration in a different direction from the projections of the outer surface 12e of the upper bearing member 12. In the illustrated embodiment, the teeth 12k of the upper bearing member 12 are configured to resist movement in a proximal direction along the longitudinal axis L1 of the upper bearing member 12, but provide less resistance to movement in a distal direction along the longitudinal axis. Similarly, the teeth 14k of the lower bearing member 14 are configured to resist movement in a distal direction along the longitudinal axis L1 of the lower bearing member 14, but provide less resistance to movement in a proximal direction along the longitudinal axis. With this configuration, the teeth 12k, 14k simultaneously resist movement in both the distal and proximal directions when the outer surfaces 12e, 14e of the bearing members are firmly engaged with the adjacent vertebrae. Alternatively, the projections may be configured to be direction-neutral, or may all be configured to resist movement in the same direction. Other structures known for fixing an implant in the intervertebral space may also be used, such as screws, fins, spikes, deployable or rotatable fixation members, adhesives, and the like.

The expansion mechanism 15 in the present embodiment is preferably configured to occupy a relatively small portion of the interior of the interbody device 10, in order to maximize the volume available for introduction of osteoconductive material within the device 10. In addition, the expansion mechanism 15 is preferably configured to permit insertion of osteoconductive material before insertion of the device into the intervertebral space, after insertion of the device but before the device is expanded, as well as after the device 10 is expanded within the intervertebral space. In the disclosed embodiment, the expansion mechanism occupies only the interior space adjacent the perimeter of the interbody device, except at the proximal trailing end 12d, 14d, which is open, so as to allow the insertion of bone-growth material or other components of the device, such as a plug member or spacer 24.

Figure 7:
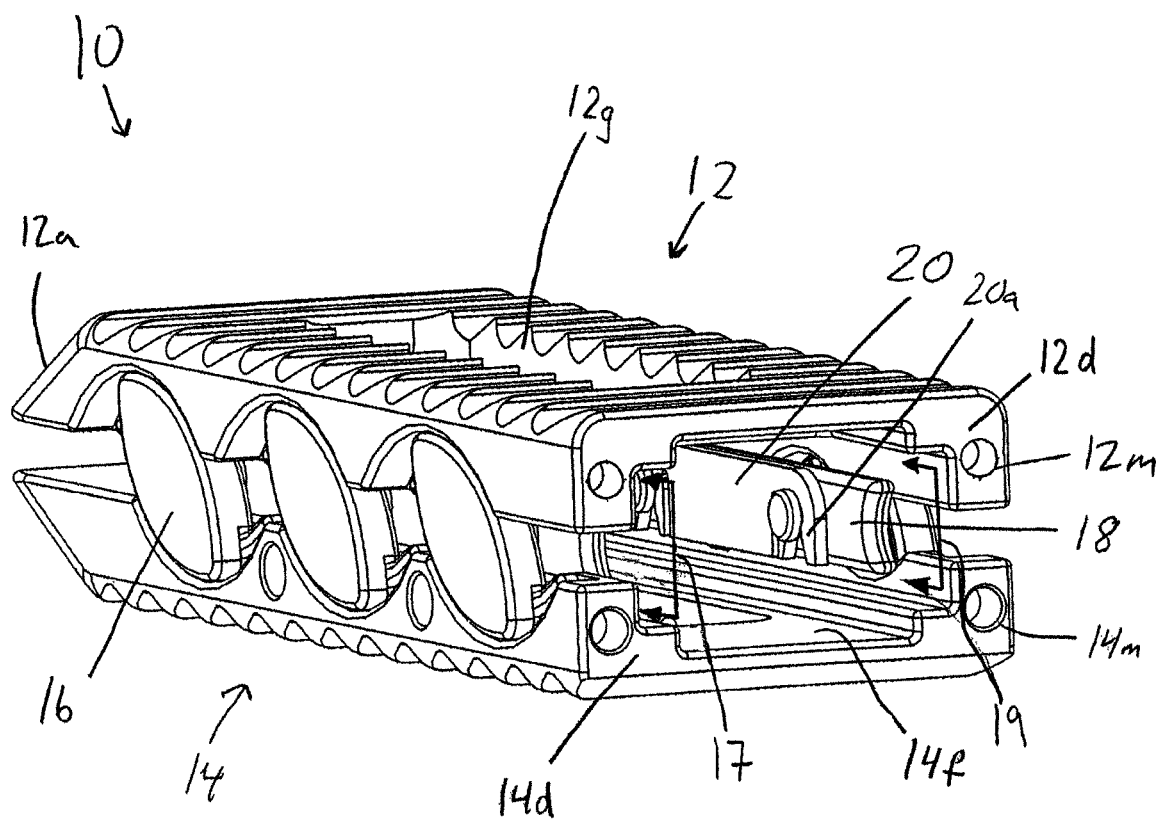
FIG. 7 is a perspective view of the interbody device of FIG. 1 in the fully expanded configuration showing the proximal end of the device.

The expansion mechanism 15 includes elliptical or football-shaped cams or slide members 16 having opposing arcuate outer edges 16d, and being interconnected via a u-shaped yoke or carriage member 18. Each slide member 16 includes a shaft portion 16a which is rotatably captured within throughbores 18a of the carriage member 18 via retainer members 20, 22 located along the interior surfaces of the legs or side walls of the carriage member 18. The carriage member legs and retainer members 20, 22 are received in interior recessed, side channel portions 17, 19 formed by the interior surfaces along the sides 12b, 12c, 14b, 14c of the bearing members 12, 14 on either side of the pathway through the device 10 circumscribed by the upper and lower through-openings 12g, 14g. The retainer members 20, 22 have clip portions 20a, 22a for receiving a recessed portion of shaft portion 16a via a snap fit for retaining the slide members 16 while allowing them to rotate with respect to the retainer members 20, 22 and the carriage member 18. The carriage member 18 causes the slide members 16 to move and rotate in unison, such that the expansion and contraction of the interbody device is accomplished in an even and controlled manner. The carriage member 18 also provides a containment surface between the upper and lower bearing members 12, 14. In particular, as seen in FIGS. 6 and 7, each leg of the u-shaped carriage member 18 surrounds the interior of the intervertebral device at the distal leading ends 12a, 14a and at the opposing lateral sides 12b, 12c, 14b, 14c. When the bearing members are in the expanded position, the carriage member fills at least a portion of the gap between the bearing members 12, 14. This is particularly useful for retaining bone growth material within the intervertebral device, especially material that is relatively fluid or free flowing. Other ways of enclosing the interior space of the interbody device could be used, such as bellows.

Figure 4:
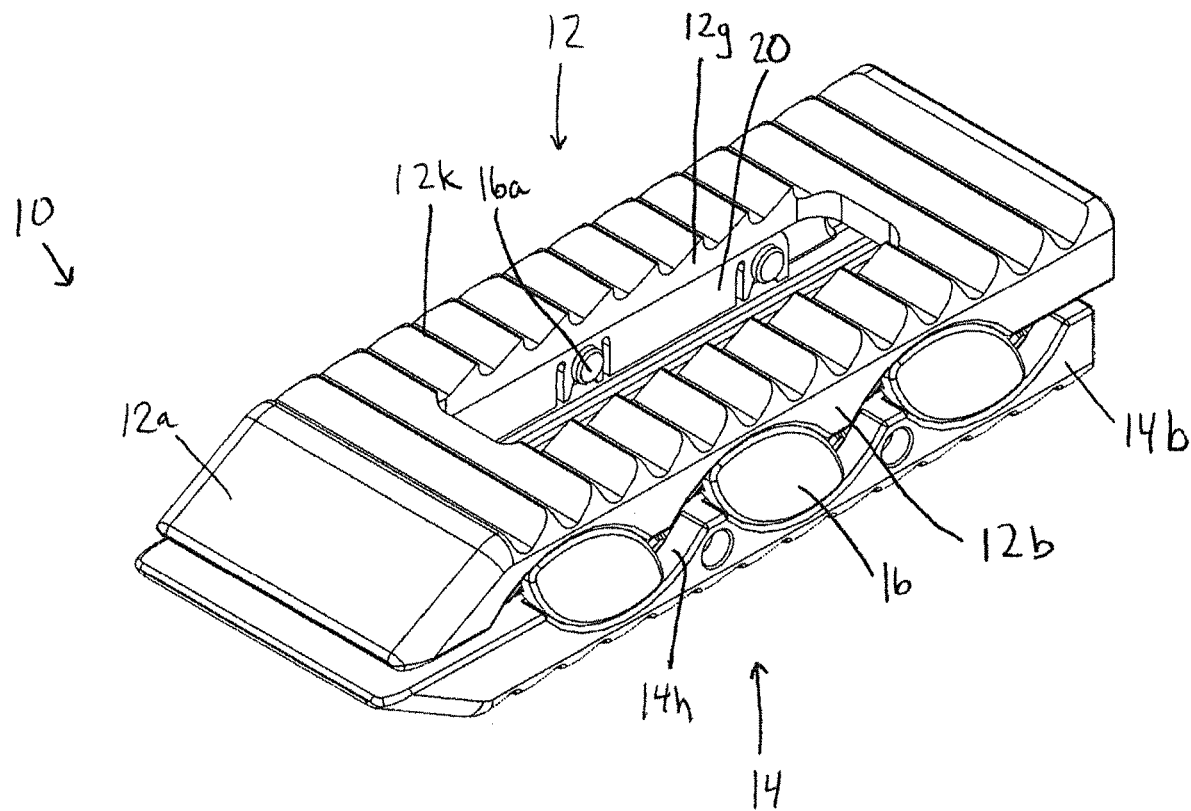
FIG. 4 is a perspective view of the interbody device of FIG. 1 in a partially expanded configuration.
Figure 5:
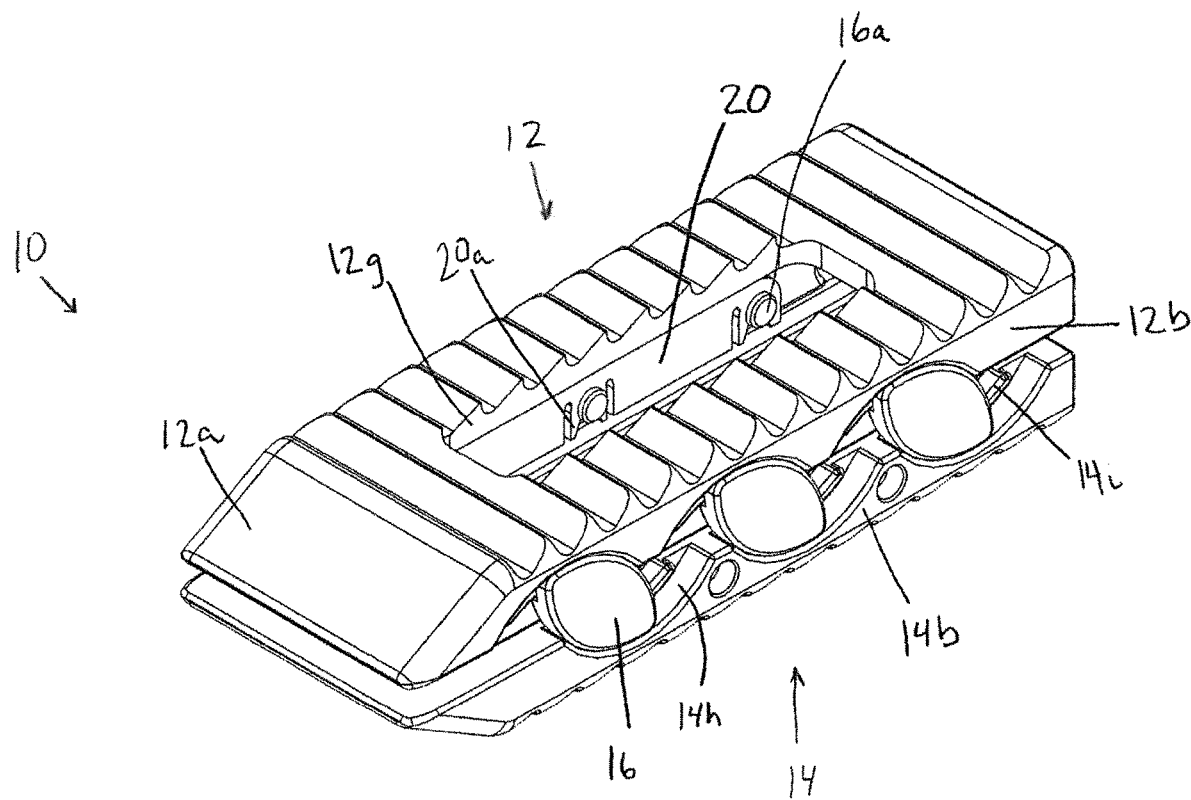
FIG. 5 is a perspective view of the interbody device of FIG. 1 in a fully expanded configuration.
Figure 10:
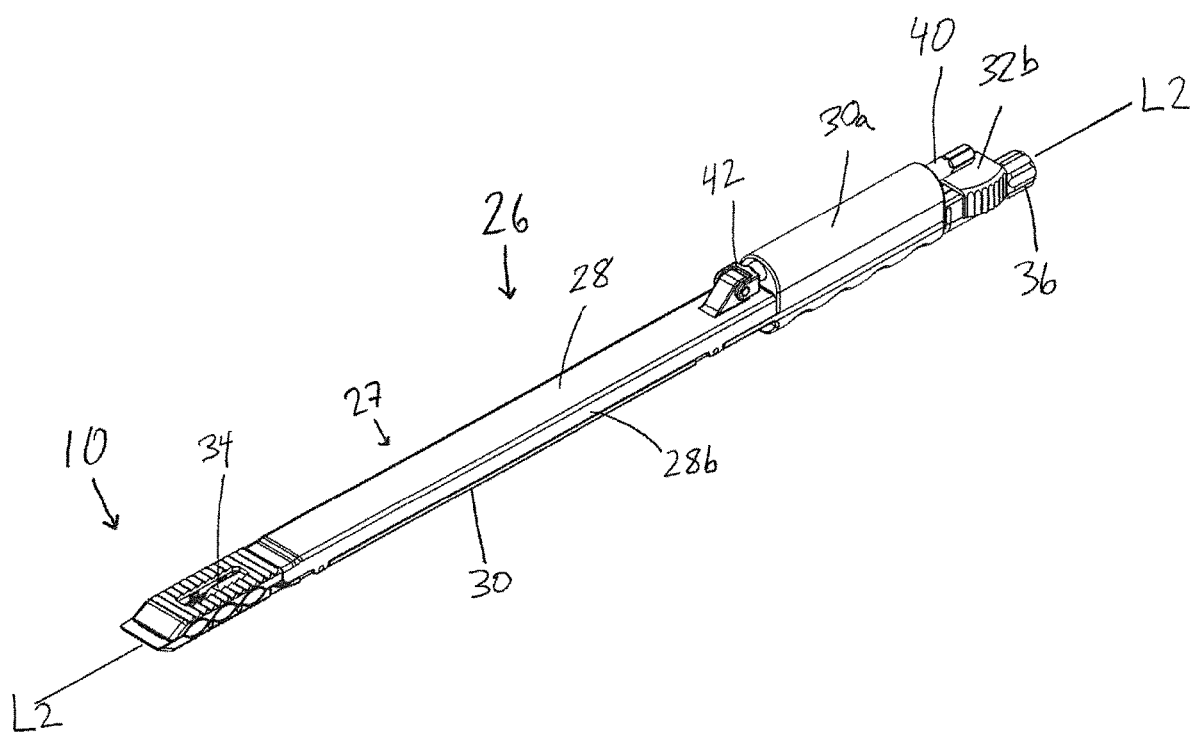
FIG. 10 is a perspective view of the interbody device held by an insertion tool in accordance with another aspect of the invention.
Figure 11:
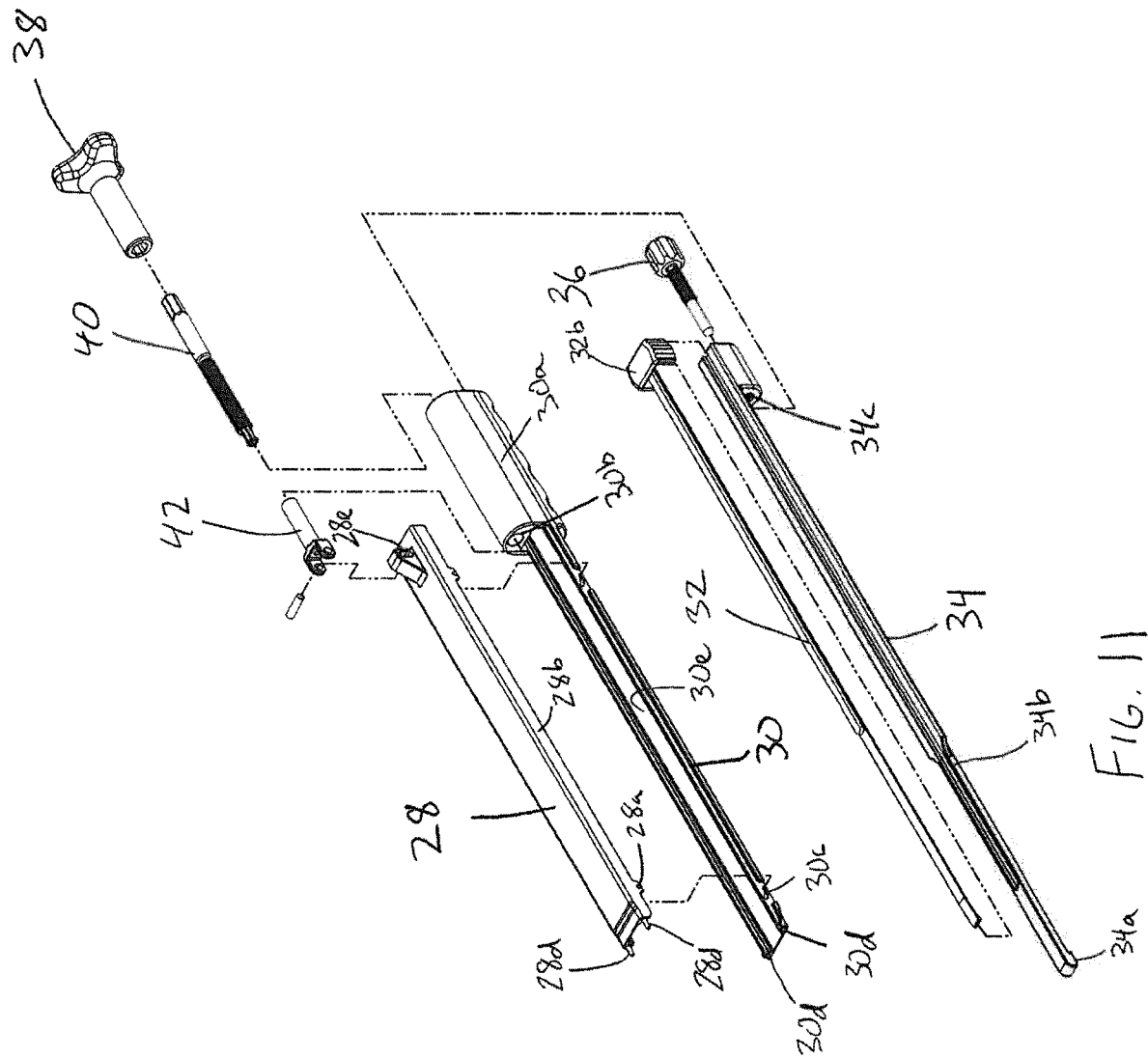
FIG. 11 is an exploded view of the insertion tool of FIG. 10.
Figure 12:
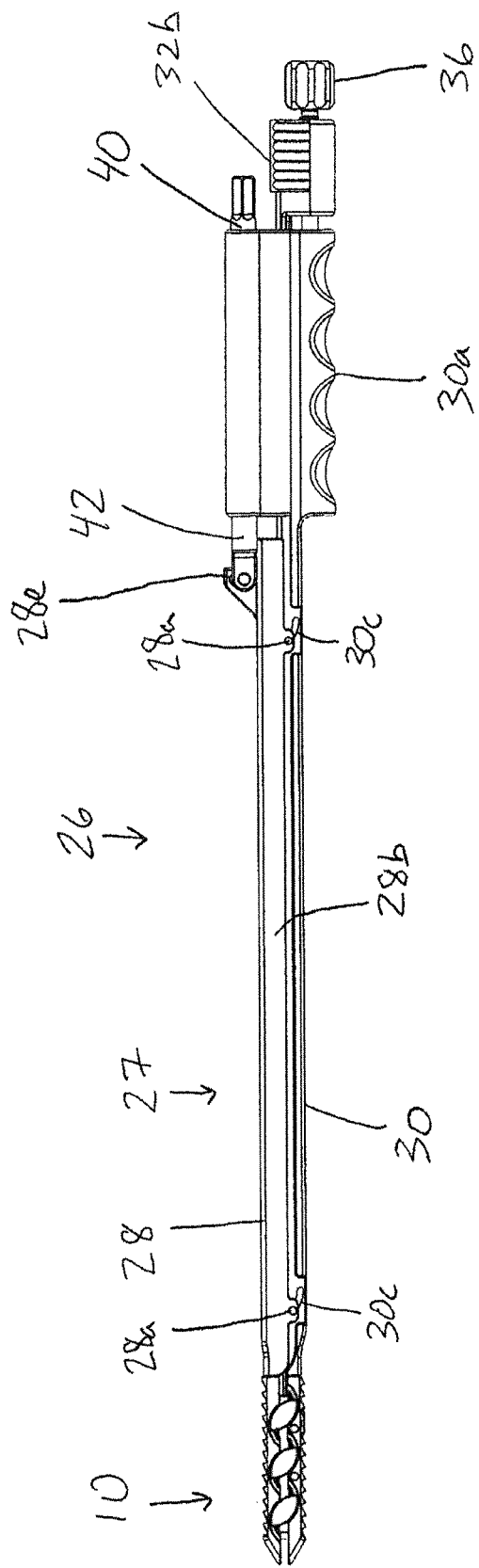
FIG. 12 is a side view of the insertion tool and interbody device of FIG. 10.

Each slide member 16 resides in corresponding arcuate recesses 12h, 14h along the lateral sides 12b, 12c, 14b, 14c of the upper and lower bearing members 12, 14. Each slide member 16 includes a pair of opposing upper and lower arcuate ridges 16b, 16c along the outer perimeter of the inner facing surface of the slide member 16. The arcuate ridges 16b, 16c travel within arcuate channels defined by the arcuate recesses 12h, 14h and corresponding arcuate ridges 12i, 14i, respectively. The operation of the slide members is shown in FIGS. 1, 4, and 6. As shown in FIG. 1, the upper member 12 rests proximally offset along axis L1 from the lower member 14 in the compact configuration. Using an insertion tool as shown in FIGS. 10-12, the upper member 12 is urged distally and upwardly away from the lower member 14. The slide members 16 shift distally and rotate clockwise, with the opposite arcuate outer edges 16d of the slide cam members 16 camming against the arcuate recesses 12h, 14h of the bearing members 12, 14 and the slide members 16 following the arcuate path defined by the arcuate recesses 12h, 14h in the upper and lower bearing members 12, 14. The carriage member 18 also shifts along with the slide members 16 in a corresponding manner.

The slide members 16 and the corresponding mating structure of the upper and lower members 12, 14 are preferably sized and configured to cause the upper and lower members to reach an aligned orientation relative to each other along the proximal-distal direction at the fully-expanded configuration, as shown in FIG. 6. In one embodiment, the fully-expanded configuration height is 2 mm greater than the compact configuration. In the disclosed embodiment, the interbody device 10 in the compact configuration has a height of approximately 8.5 mm, such that the fully expanded configuration has a height of 10.5 millimeters. However, the bearing members could be sized such that the compact configuration has a different height, such as 8 or 9 mm. In addition, different sized bearing members, slide members, and corresponding mating structure may be used to achieve different variations in height and levels of expansion. Although the disclosed embodiment uses six slide members, more or fewer slide members may be used in different proportions, such as 2, 4, or 8. Typically, using more slide members will result in lower stresses on each slide member, as well as the bearing members 12, 14. The slide members may also have different configurations. For example, instead of arcuate outer surfaces 16d, the slide members may have a linear or wedge-like configuration. Further, the expansion mechanism could be omitted and expansion of the interbody device could be accomplished primarily or solely by the insertion tool or a separate spacer.

The interbody device bearing members 12, 14 and the expansion mechanism 15 are sized and configured to provide a cavity within the interbody device 10 that is substantially free from encroachment by the expansion mechanism 15. In the disclosed embodiment, the through-openings 12g, 14g have a rectangular shape, and the expansion mechanism 15 occupies the space between the bearing members 12, 14 outside of the perimeters of the through-openings 12g, 14g such as in the channels 17, 19 extending alongside the through-openings 12g, 14g, shown in FIG. 7, such that the expansion mechanism 15 is entirely external to the through-openings 12g, 14g and the space between them, such that there is an uninterrupted void between the outer surfaces of the upper and lower bearing members to promote boney ingrowth between the adjacent vertebrae. It is preferable, but not necessary, that the void be maximized in size to accommodate a greater proportion of biologic material for promoting fusion. To this end, when the bearing members are fully expanded, it is preferable that the through-openings 12g, 14g are in substantial axial alignment in order to provide a prismatic void having upper and lower bases defined by the through-openings 12g, 14g between the outer bearing surfaces 12e, 14e to provide a substantially straight path for boney ingrowth. However, some offset between the through-openings 12g, 14g is acceptable, such as when the bearing members are only partially expanded, such that the upper and lower bearing members 12, 14 are offset from one another along the longitudinal axis L1 of the interbody device, as shown in FIGS. 1 and 4.

The interbody device is preferably configured to allow for insertion of osteoconductive material, such as natural or synthetic bone grafts, including NANOSS® Bioactive 3D, an advanced bone graft composed of nano-structured hydroxyapatite granules and an open structured engineered collagen carrier in a strip format, available from Pioneer Surgical Technology, Inc. Other biologics may be used, such as NANOSS® Bioactive or NANOSS® Bioactive Loaded, available from Pioneer Surgical Technology, Inc., the latter being a flowable biologic material delivered via a syringe. Other known osteoconductive materials may also be used.

The bone-growth material may be inserted into the cavity of the intervertebral device prior to insertion of the device into the intervertebral space. Alternatively, the bone-growth material may be inserted into the interbody device after insertion of the device into the intervertebral space, either before or after expansion of the bearing members. As shown in FIG. 7, the trailing ends 12d, 14d of the upper and lower bearing members are sized and configured to provide an access opening between the bearing members 12, 14 that communicates with the interior of the interbody device 10 and the void between the through-openings 12g, 14g in the outer surfaces 12e, 14e of the upper and lower bearing members for inserting osteoconductive material into the void through the recess. As will be discussed below, the inner facing surfaces 12f, 14f of the bearing members 12, 14 are sized and configured to receive a plug member 24 which is preferably operable as a spacer to maintain the desired spacing between the upper and lower bearing members 12, 14, and also to retain the biologic material within the body of the intervertebral device 10.

Figure 8:
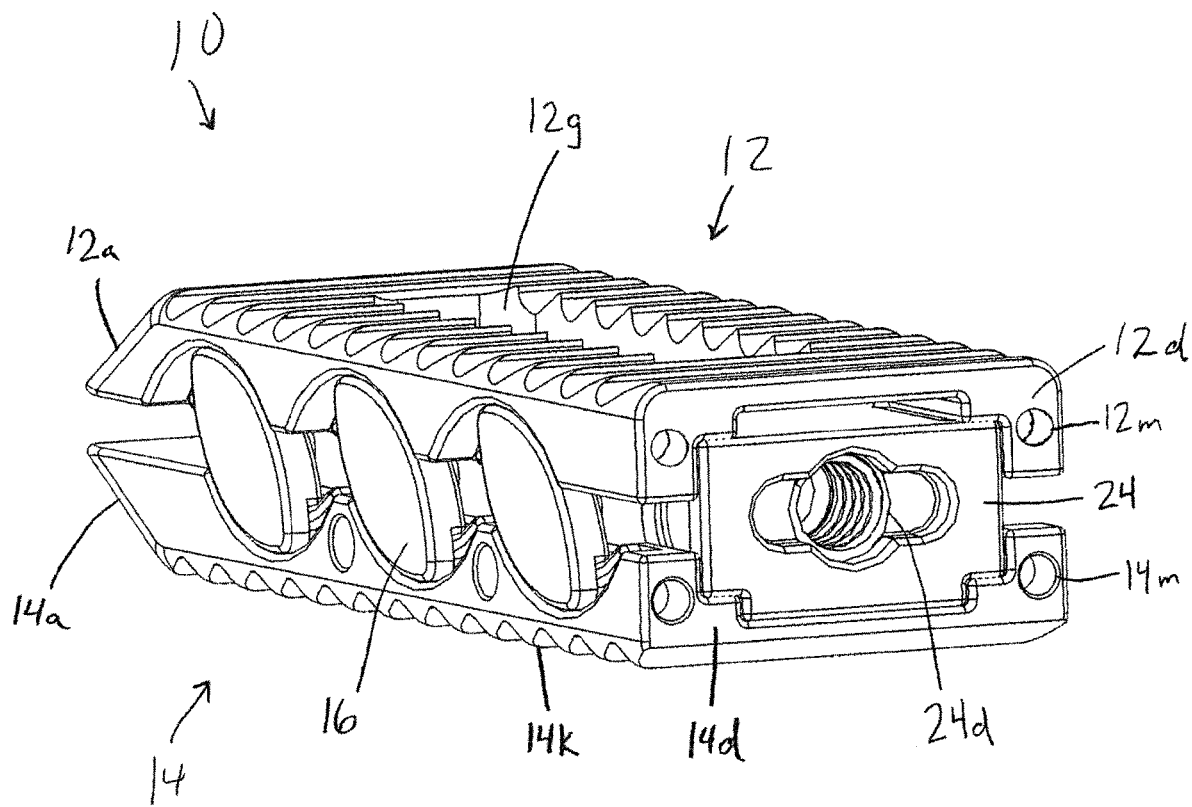
FIG. 8 is a perspective view of the interbody device of FIG. 1 in the fully expanded configuration with a plug member inserted into the interbody device in a first orientation.
Figure 9:
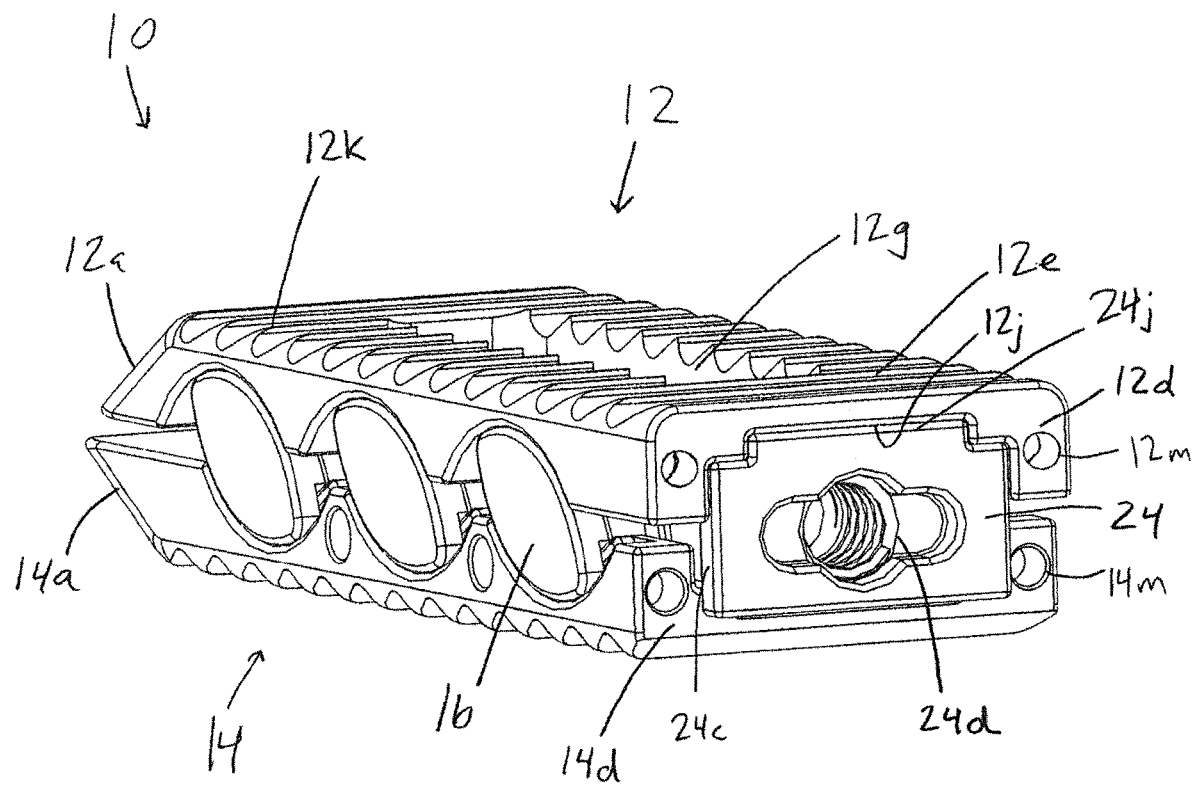
FIG. 9 is a perspective view of the interbody device of FIG. 1 in the partially expanded configuration with the plug member inserted into the interbody device in a second orientation rotated 180 degrees from the first orientation.

A plug member 24 is configured to retain bone-growth material within the interbody device 10, as well as to fix the height of the device to keep the interbody device 10 in the expanded configuration after the insertion tool 26 is removed from the interbody device 10. In one form, the height of the expandable interbody device may be selected and fixed via insertion of the plug member 24 configured to keep the interbody device in a plurality of different expanded configurations corresponding to different heights of the interbody device depending on the orientation in which the plug member is inserted into the interbody device. Accordingly, the plug member 24 may be configured such that it is operable to maintain a plurality of different expanded configurations of the interbody device. For example, the plug member 24 may be inserted in a first orientation which maintains a first distance between the upper and lower bearing members 12, 14. The plug member 24 may alternatively be inserted in a second orientation different from the first that maintains a second distance between the upper and lower bearing members 12, 14. In the embodiment shown in FIGS. 7-9, the plug member is rotated about its longitudinal axis 180 degrees to alternate between the two orientations. In this embodiment, the first orientation is shown in FIG. 9, which corresponds to an expansion of the bearing members of 1 mm, and the second orientation is shown in FIG. 8, in which the plug member is rotated 180 degrees, corresponding to an expansion of 2 mm. This feature is achieved through the stepped interior surfaces 12f, 14f, recessed portion 12j, mating raised pedestal portion 24j, and the corresponding elongate rail portions 24a, 24b of the plug member 24, as shown in FIGS. 2 and 3.

In the first orientation of the plug member 24 shown in FIG. 9, the raised portion 24j resides within the corresponding recessed portion 12j of the interior surface 12f (see FIG. 3). The narrower pair of rail portions 24a of the plug member fit between the stepped portions of interior surface 14f of the lower bearing member 14. As seen in FIG. 9, the plug member has a distal flange portion 24c which in the first orientation abuts the proximal trailing edge 14d of the lower bearing member 14, keeping the plug member 24 from being completely inserted into the lower bearing member 14. In the second orientation of the plug member 24 shown in FIG. 8, the wider rail portions 24b rest on top of the stepped portions of interior surface 14f of the lower bearing member 14, and the raised portion 24j of the plug member 24 resides between the stepped portions. Plug member 24 includes a threaded recess 24d at its proximal end for mating with an insertion tool.

The plug member 24, may be configured to hold a osteoconductive material, such that the bone-growth material is inserted together with the plug 24 into the interior of the interbody device 10 at the same time. Alternatively, the bone growth material may be inserted separately from the plug member 24.

An insertion tool is provided for inserting the interbody device 10 into an intervertebral space and for expanding the device after insertion. In addition, the tool also provides an enclosed pathway for inserting bone growth material into the interbody device as well as other components of the interbody device, such as a plug member or spacer for inserting bone-growth material or fixing the height of the interbody device.

In the embodiment shown in FIGS. 10-14, the insertion tool includes an elongate hollow shaft assembly 27, which is formed by upper and lower shaft members 28, 30 that are shiftably connected and configured to distract apart from one another. The lower shaft member 30 is configured to engage the lower bearing member 14 of the interbody device 10 and the upper shaft member 28 is configured to shift the upper bearing member 12 of the interbody device 10 apart from the lower bearing member 14 via an actuator. Each shaft member 28, 30 has a generally u-shaped cross section, with the side walls 30c of the lower shaft member 30 sized to fit inside of the side walls 28b of the upper shaft member 28 such that the side walls 28b of the upper shaft member overlap with the side walls 30c of the lower shaft member. Together, the shafts 28, 30 define a generally rectangular void between the shafts, which forms an enclosed pathway through the shaft assembly 27 that is accessible through a recess 30d in the proximal end of the handle 30a. The enclosed pathway extends through the handle 30a at the proximal end of the tool all the way to the distal end of the shaft assembly 27 to provide a protected path for the insertion of materials into the interior of the interbody device 10 while the insertion tool 26 is engaged with the device 10. Small gaps or openings may be present while still achieving the desired function of providing an enclosed path. Accordingly, the words "enclosed," "protected," and the like are intended to include tools that include some small gaps or openings. The hollow shaft assembly 27 is sized and configured to substantially match the height and width of the interbody device 10, as shown in FIG. 10, so that the system provided by the interbody device 10 and tool 26 is minimally invasive.

Handle 30a is operably connected to an actuator configured to move the upper shaft member 28 with respect to the lower shaft member 30. The actuator includes a knob 38, which is removably connected to the proximal end of a partially threaded drive shaft 40. A push rod 42 is rotatably connected to the distal end of the drive shaft 40, but is configured not to be rotated by rotation of the drive shaft. The push rod 42 is connected at its distal end to the upper shaft member 28 via a pin disposed in a vertically oriented slot 28e to allow the upper shaft member 28 to move transversely (i.e., up and down) with respect to the longitudinal axis of the push rod 42. The drive shaft 40 fits within a threaded recess 30b in the handle portion 30a that is aligned with a longitudinal axis L2 of the tool 26, such that rotation of the drive shaft 40 causes the drive shaft and the push rod 42 to move axially, either proximally or distally.

The hollow shaft assembly 27 is configured to expand between a compact insertion configuration to an expanded configuration to expand the interbody device 10 and increase the circumference of the enclosed pathway through the shaft assembly 27. The upper shaft 28 is configured to move both axially and upwardly with respect to the lower shaft 30 such that the shaft members distract apart from one another to increase the circumference of the enclosed pathway through the shaft assembly 27. The upper shaft includes four pins 28a, two near each end of the shaft 28 that are connected to the side walls 28b of the upper shaft 28 and extend inwardly toward the opposite side wall 28b. These pins 28a are captured within four corresponding arcuate grooves 30c formed in the lower shaft 30, with two near each end of the shaft 30. The arcuate grooves 30c are configured to cause the upper shaft member 28 to shift in a manner that matches the movement of the upper bearing member 12. Thus, when the upper shaft member 28 is pushed in the longitudinal direction by the push rod 42, it moves along a path corresponding to the shape of the arcuate grooves 30c. This causes a corresponding movement of the upper bearing member 12 when the interbody device 10 is connected to the distal end of the insertion tool 26.

Figure 13:
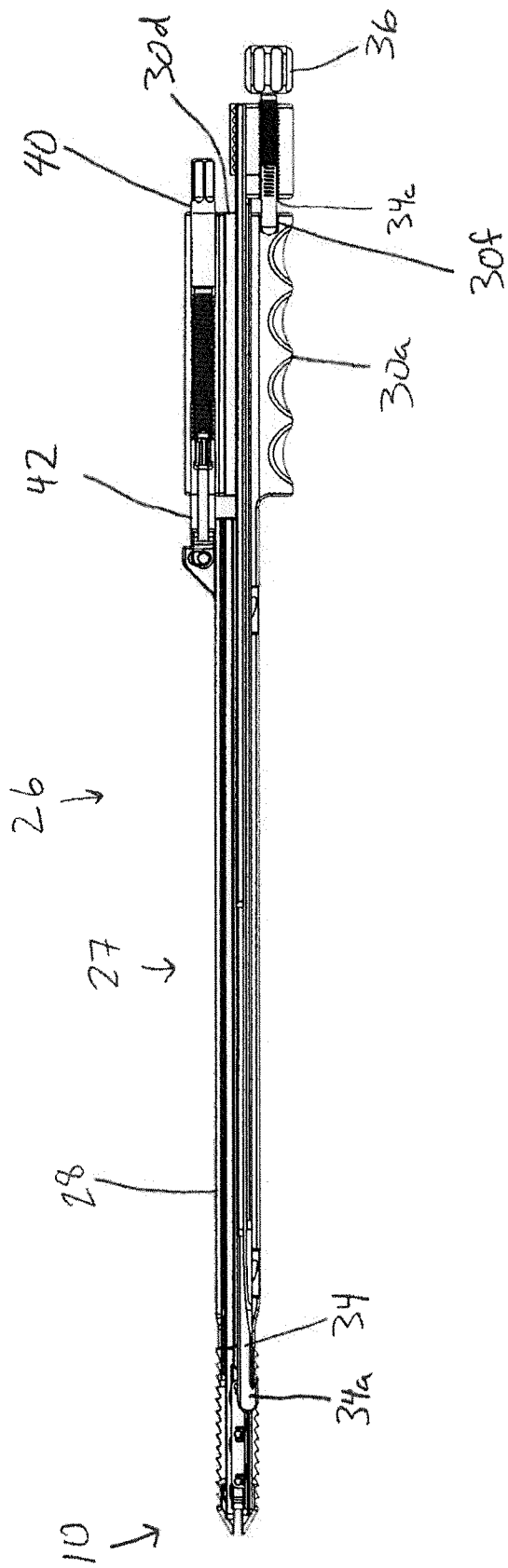
FIG. 13 is longitudinal cross-sectional view of the insertion tool and interbody device of FIGS. 10.
Figure 14:
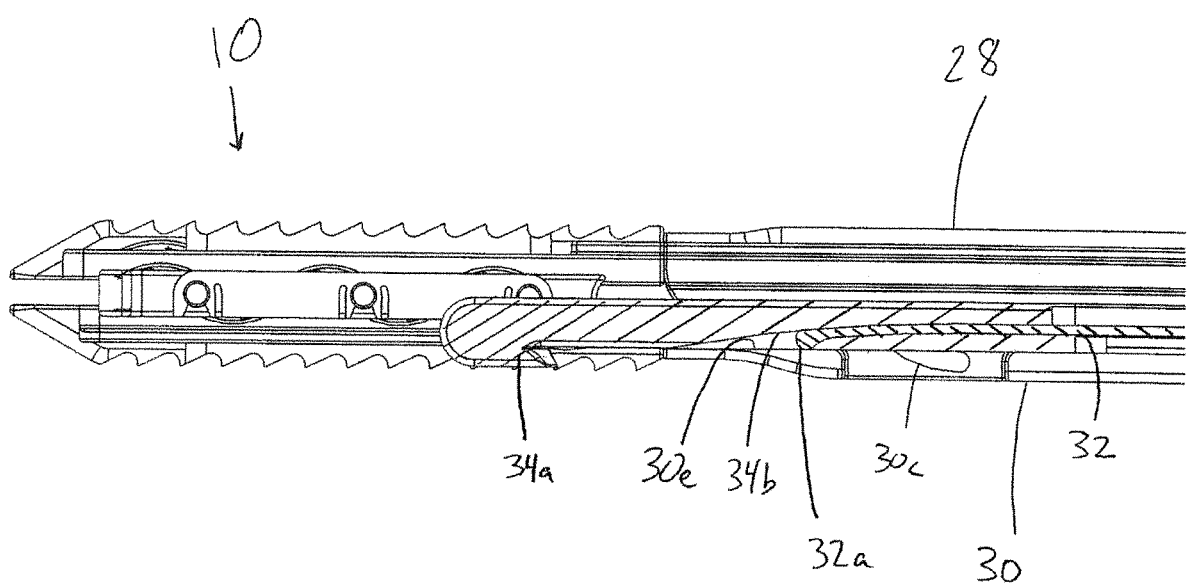
FIG. 14 is an enlarged cross-sectional view of FIG. 13, showing the configuration of the gripping and release shafts.

The inserter tool 26 is configured to hold the interbody device 10 via a gripping shaft 34 having an interbody device engaging portion in the form of a hooked distal end 34a. The gripping shaft 34 is disposed within the hollow shaft assembly 27 for gripping the expandable interbody device 10 and holding the interbody device against a distal end of the hollow shaft assembly 27. The hook 34a is configured to engage the lower bearing member 14 as shown in FIGS. 13 and 14. Specifically, the hook 34a is inserted through the opening in the proximal end of the interbody device 10 and engages a hook engaging surface 141 at the proximal edge of the through-opening 14g. Hook engaging surface 141 is sloped proximally from the inner surface 14f to the outer surface 14e to conform with the hook 34a so that the hook may securely grip the lower bearing member 14 against the distal end of the shaft assembly 27.

The gripping shaft 34 is operable to shift into and out of engagement with the interbody device 10 via an actuator. As shown in FIG. 11, the actuator 36 takes the form of threaded shaft having a knob at its proximal end. The gripping shaft actuator 36 resides in a threaded throughbore 34c disposed at the proximal end of the gripping shaft 34. The distal end of the gripping shaft actuator is rotatably captured in a blind recess 30f in the proximal end of the handle 30a. In operation, rotating the knob of the actuator 36 shifts the gripping shaft 34 axially in the distal or proximal directions along the longitudinal axis L2. Accordingly, after the gripping shaft 34 is inserted into the interbody device 10, the device 10 may be gripped and held to the distal end of the inserter 26 by rotating the actuator knob 36 to shift the gripping shaft 34 in the proximal direction until the hooked end 34a firmly engages with the engagement portion 141 of the lower bearing member 14 and captures the proximal end of the lower bearing member 14 between the hooked end 34a and the distal end of the lower shaft 30.

The distal ends of the upper and lower shaft members 28, 30 each include a pair distally extending prongs 28d, 30d for engaging with mating recesses 12m, 14m located on the proximal trailing end of the upper and lower bearing members. In an alternative embodiment, one or both sides 12b, 12c, 14b, 14c of the bearing members 12, 14 may be provided with mating structure, such as recesses 14n for engaging with an alternate insertion tool.

The gripping shaft 34 includes an elongate recess 34b which extends along most of the length of the gripping shaft. Release shaft 32 is configured for sliding engagement with the gripping shaft 34 within the elongate recess 34b. The release shaft 32 has a distal end 32a configured to release the hooked distal end 34a of the gripping shaft 34 from the interbody device 10 when the release shaft 32 is shifted relative to the gripping shaft 34. In particular, as shown in FIG. 14, the elongate recess 35 ends at an opening on the underside of the gripping shaft near the distal end thereof. When the release shaft is urged distally using the knob 32b, the distal end 32a of the release shaft 32 engages against the inside surface 30e of the lower shaft member 30 and against the upper surface of the elongate recess 34b, causing the gripping shaft 34 to be urged upwardly away from the lower shaft member 30. If the gripping shaft is moved sufficiently distally such that the hook member 34a may clear the hook engaging surface 141, the gripping shaft 34 may then be pulled out from the interior of the interbody device 10 and then removed completely from the inserter tool 26 by pulling the gripping shaft 34 and release shaft 32 out through the recess 30d in the proximal end of the handle 30a. The inserter tool shaft assembly 27 and interbody device 10 may need to be in an expanded configuration to allow removal of the gripping shaft and release shaft 32. Once the gripping and release shafts 32, 34 are removed from the hollow shaft assembly 27, the tool 26 may be kept in place engaged with the interbody device 10, and osteoconductive material (or additional osteoconductive material) may be inserted into the interior of the interbody device 10 through the body of the insertion tool 26. The shaft assembly 27 provides a cannula-like passage for safe and easy insertion of osteoconductive material and other components, such as plug 24.

The interbody device 10 and insertion tool 26 may be sized and configured such that the device 10 may be inserted in many different approaches with respect to the spine, such as anterior, anterolateral, lateral, posterolateral, or posterior approaches. A lateral approach is advantageous for purposes of stability of the vertebral joint, as the interbody device will be oriented with its length along the lateral axis of the spine, allowing the outer surfaces of the interbody device to be sized to engage a relatively larger surface area of the inner facing surfaces of the adjacent vertebrae and/or engage more of the harder bone or tissue of the inner vertebral surfaces away from the center of the vertebrae than would be possible in other approaches or orientations. In another method, the device and tool system can be sized and configured to implant the device 10 through Kambin's triangle. Kambin's triangle is defined as a right triangle over the dorsolateral disc. The hypotenuse of Kambin's triangle is the exiting nerve root, the base being the superior border of the caudal vertebral body, and the height is the traversing nerve root. (See Park et al, Kambin's Triangle Approach of Lumbar Transforaminal Epidural Injection with Spinal Stenosis, Annals of Rehabilitation Medicine, Dec. 30, 2011.) With such an approach, the intervertebral disc is prepared for implantation by creating an opening in the annulus of the intervertebral disc for insertion of the interbody device within the boundaries defined by Kambin's triangle. Such an approach is advantageous because the device may be implanted without needing to remove any portion of the vertebral bone prior to insertion, simplifying the method of inserting the device and reducing trauma to the patient. In one form, the interbody device 10 is about 18 mm wide, 36-38 mm long, with an unexpanded height of around 8 mm. Other dimensions are certainly contemplated depending on the application, surgical approach, and implant site characteristics.

A method of inserting an expandable intervertebral device includes preparing an intervertebral disc for implantation of the expandable interbody device, inserting the interbody device into the intervertebral space with an insertion tool, expanding the interbody device into an expanded configuration with the insertion tool, and inserting osteoconductive material through an enclosed path of the insertion tool into the interbody device while the insertion tool is engaged with the interbody device. As discussed above, a plug member may be inserted into the interbody device for keeping the osteoconductive material within the interbody device. The height of the expandable device may be fixed via insertion of the plug member to keep the interbody device in the expanded configuration after the insertion tool is removed from the interbody device. The plug member may be configured to keep the interbody device in a plurality of different expanded configurations corresponding to different heights of the interbody device depending on the orientation in which the plug member is inserted into the interbody device. Expanding the interbody device into the expanded configuration may also include expanding the circumference of the enclosed path in the insertion tool.

Any known materials appropriate for implantation into the human body may be used for the interbody device. However, it is preferred to use a polymer such as PEEK for the bearing members 12, 14 and titanium for components of the expansion mechanism 15. Coatings, such as hydroxyapatite (HA), may be used to promote bone growth to the surfaces of the interbody device 10. Other materials may be used, as is well known in the art.

The above description is not intended to be limiting on the invention, but is merely illustrative of preferred embodiments of this invention. Additional objects, features and advantages of the present invention will be apparent to those of ordinary skill in the art by referring to the above description in connection with the accompanying drawings.

What is claimed is:

1. An expandable intervertebral device for implantation within an intervertebral space between adjacent vertebrae, the expandable intervertebral device comprising:
    upper and lower bearing members each having a bone-engaging outer surface; and
    an expansion mechanism operably connected to the upper and lower bearing members for allowing the bearing members to shift between a compact configuration and an expanded configuration;
    wherein the expansion mechanism comprises at least one rotatable slide member having arcuate surfaces that are in operable engagement with the upper and lower bearing members, the at least one rotatable slide member configured to rotate when the bearing members are shifted between the compact and expanded configurations;
    wherein the upper and lower bearing members each have lateral sides extending between a distal leading end and a trailing proximal end, and the at least one rotatable slide member is positioned along one of the lateral sides of the upper and lower bearing members;
    wherein the at least one rotatable slide member has an axis of rotation that extends laterally with respect to the upper and lower bearing members;
    further comprising a plurality of slide members including the at least one slide member, wherein the plurality of slide members are interconnected via a carriage member;
    wherein the carriage member is u-shaped and extends between opposing lateral sides of the upper and lower bearing members to operably connect the plurality of slide members and provide a containment surface between the upper and lower bearing members.

2. The expandable intervertebral device of claim 1, wherein the arcuate surfaces of the at least one slide member include an upper arcuate surface in engagement with the upper bearing member and a lower arcuate surface in engagement with the lower bearing member.

3. The expandable intervertebral device of claim 2, wherein the upper bearing member includes a corresponding arcuate surface for engaging with the upper arcuate surface of the at least one slide member, and the lower bearing member includes a corresponding arcuate surface for engaging with the lower arcuate surface of the at least one slide member.

4. The expandable intervertebral device of claim 1, wherein the at least one slide member has an oval shape.

5. The expandable intervertebral device of claim 1, wherein the upper and lower bearing members each have an inner facing surface and a through-opening extending between the bone-engaging outer surface and the inner facing surface thereof, and wherein the expansion mechanism is spaced from the through-opening in each of the upper and lower bearing members so that the through-openings provide an uninterrupted void between the outer surfaces of the upper and lower bearing members to promote boney ingrowth between the adjacent vertebrae.

6. The expandable intervertebral device of claim 1, wherein the bone-engaging outer surface of the upper bearing member comprises projections that are configured to resist migration in one direction, and the outer surface of the lower bearing member comprises projections that are configured to resist migration in a different direction from the projections of the outer surface of the upper bearing member.

7. The expandable intervertebral device of claim 1, further comprising a plug member sized and configured to be received between the upper and lower bearing members in the expanded configuration thereof, the plug member operable to keep the upper and lower bearing members in the expanded configuration thereof.

8. The expandable intervertebral device of claim 1, wherein the at least one slide member is configured so that when the upper and lower bearing members are shifted from the compact configuration to the expanded configuration, the at least one slide member is caused to rotate to stay in engagement with and support the upper and lower bearing members in the expanded configuration.

9. A method of inserting an expandable interbody device in an intervertebral space, comprising:
    preparing an intervertebral disc for implantation of the expandable interbody device;
    inserting the expandable interbody device into the intervertebral space with an insertion tool;
    expanding the expandable interbody device into an expanded configuration with the insertion tool;
    inserting osteoconductive material through a hollow shaft of the insertion tool into the expandable interbody device while the insertion tool is engaged with the expandable interbody device;
    wherein the expandable interbody device is expanded into the expanded configuration by expanding the circumference of the hollow shaft of the insertion tool;
    wherein the expandable interbody device includes upper and lower bearing members and inserting the expandable interbody device includes positioning the upper and lower bearing members in an offset configuration with one of the bearing members leading the other into the intervertebral space.

10. The method of claim 9, further comprising inserting a plug member into the expandable interbody device for keeping the osteoconductive material within the expandable interbody device.

11. The method of claim 9, wherein the plug member is inserted into the expandable interbody device through the hollow shaft of the insertion tool.

12. The method of claim 9, further comprising fixing the height of the expandable interbody device via insertion of a plug member therein to keep the expandable interbody device in the expanded configuration after the insertion tool is removed from the expandable interbody device.

13. The method of claim 9, wherein expanding the expandable interbody device into the expanded configuration comprises shifting the upper bearing member apart from the lower bearing member.

14. The method of claim 9, further comprising selecting the height of the expandable interbody device via insertion of a plug member configured to keep the expandable interbody device in a plurality of different expanded configurations corresponding to different heights of the expandable interbody device depending on the orientation in which the plug member is inserted into the expandable interbody device.

15. The method of claim 9, wherein the step of preparing an intervertebral disc for implantation comprises removing a lateral portion of the annulus of the intervertebral disc for insertion of the expandable interbody device laterally into the intervertebral space.

16. The method of claim 9, wherein expanding the circumference of the hollow shaft of the insertion tool includes shifting an upper shaft member relative to a lower shaft member.

17. A system for implanting an expandable interbody device between adjacent upper and lower vertebrae with an insertion tool, the system comprising:
the expandable interbody device having upper and lower bearing members and an expansion mechanism comprising at least one slide member having arcuate surfaces operable to engage the upper and lower bearing members, the at least one slide member configured to rotate as a result of the upper and lower bearing members being shifted between compact and expanded configurations;
an opening at a proximal end of the upper and lower bearing members for receiving osteoconductive material or additional components into an interior of the expandable interbody device; and
the insertion tool being configured to hold, insert, and expand the expandable interbody device and having a hollow shaft for allowing insertion of osteoconductive material or additional components into the interior of the expandable interbody device while the insertion tool is engaged with the upper and lower bearing members of the expandable interbody device.

18. The system of claim 17, wherein the hollow shaft is a hollow shaft assembly having an enclosed pathway extending through the shaft assembly to the opening in the proximal end of the expandable interbody device, wherein the hollow shaft assembly comprises upper and lower shaft members that are shiftably connected to distract apart from one another, wherein each of the upper and lower shaft members extends along a longitudinal axis and the upper and lower shaft members are configured such that the longitudinal axis of the upper shaft member is generally parallel to the longitudinal axis of the lower shaft member when the shaft members are distracted apart from one another to expand the expandable interbody device.

19. The system of claim 9, wherein the upper and lower bearing members each have lateral sides extending between a distal end and the proximal end thereof;
wherein the at least one slide member is positioned along one of the lateral sides of the upper and lower bearing members and remote from the proximal end opening of the upper and lower bearing members to allow osteoconductive material or additional components to be inserted into the interior of the expandable interbody device through the opening.

20. A system for implanting an expandable interbody device between adjacent upper and lower vertebrae with an insertion tool, the system comprising:
the expandable interbody device having upper and lower bearing members and an expansion mechanism comprising at least one slide member having arcuate surfaces operable to engage the upper and lower bearing members, the at least one slide member configured to rotate as the upper and lower bearing members are shifted between compact and expanded configurations;
an opening at a proximal end of the upper and lower bearing members for receiving osteoconductive material or additional components into an interior of the expandable interbody device; and
the insertion tool being configured to hold, insert, and expand the expandable interbody device and having a hollow shaft for allowing insertion of osteoconductive material or additional components into the interior of the expandable interbody device while the insertion tool is engaged with the upper and lower bearing members of the expandable interbody device;
wherein the hollow shaft is a hollow shaft assembly having an enclosed pathway extending through the shaft assembly to the opening in the proximal end of the expandable interbody device, wherein the hollow shaft assembly comprises upper and lower shaft members that are shiftably connected to distract apart from one another, wherein each of the upper and lower shaft members extends along a longitudinal axis and the upper and lower shaft members are configured such that the longitudinal axis of the upper shaft member is generally parallel to the longitudinal axis of the lower shaft member when the shaft members are distracted apart from one another to expand the expandable interbody device;
wherein the lower shaft member is configured to engage the lower bearing member of the expandable interbody device and the upper shaft member is configured to shift the upper bearing member of the expandable interbody device apart from the lower bearing member.

* * * * *

UNITED STATES PATENT AND TRADEMARK OFFICE
CERTIFICATE OF CORRECTION

PATENT NO. : 10,779,956 B2
APPLICATION NO. : 15/645485
DATED : September 22, 2020
INVENTOR(S) : Scott J. Perrow Page 1 of 1

It is certified that error appears in the above-identified patent and that said Letters Patent is hereby corrected as shown below:

In the Claims

Claim 19, Column 13, Line 46, delete "claim 9" and insert -- claim 17 --, therefor.

Signed and Sealed this
Tenth Day of August, 2021

Drew Hirshfeld
*Performing the Functions and Duties of the
Under Secretary of Commerce for Intellectual Property and
Director of the United States Patent and Trademark Office*